(12) United States Patent
Mukherjee et al.

(10) Patent No.: US 9,364,566 B2
(45) Date of Patent: Jun. 14, 2016

(54) AQUEOUS FORMULATION FOR SELECTIVE TARGETING AND DELIVERING GENE TO CANCER CELLS

(75) Inventors: Amarnath Mukherjee, Andhra Pradesh (IN); Rajkumar Banerjee, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 806 days.

(21) Appl. No.: 12/394,578

(22) Filed: Feb. 27, 2009

(65) Prior Publication Data

US 2010/0062049 A1 Mar. 11, 2010

Related U.S. Application Data

(63) Continuation-in-part of application No. PCT/IN2007/000367, filed on Aug. 27, 2007.

(30) Foreign Application Priority Data

Aug. 29, 2006 (IN) .......................... 1936/DEL/2006

(51) Int. Cl.
| | |
|---|---|
| A61K 9/127 | (2006.01) |
| A61K 31/7052 | (2006.01) |
| A61K 47/44 | (2006.01) |
| A61K 48/00 | (2006.01) |
| A61K 35/00 | (2006.01) |
| A61K 9/00 | (2006.01) |

(52) U.S. Cl.
CPC ........... *A61K 48/0025* (2013.01); *A61K 9/0019* (2013.01); *A61K 9/1272* (2013.01)

(58) Field of Classification Search
None
See application file for complete search history.

(56) References Cited

U.S. PATENT DOCUMENTS

| | | | | | |
|---|---|---|---|---|---|
| 5,958,894 | A | * | 9/1999 | Heath et al. .................. | 514/44 R |
| 6,093,417 | A | * | 7/2000 | Petrus ........................... | 424/437 |
| 6,436,516 | B1 | * | 8/2002 | Nagashima et al. .......... | 428/201 |
| 6,503,945 | B2 | * | 1/2003 | Banerjee et al. .............. | 514/547 |

OTHER PUBLICATIONS

Roy, et al. (2001) "Androgen Receptor: Structural Domains and Functional Dynamics After Ligand-Receptor Interaction", Annals of the New York Academy of Science, 949: 44-57.*
Rogerson, et al. (2004) "Mineralocorticoid receptor binding, structure and function", Molecular and Cellular Endocrinology, 217(1-2): 203-212.*
Joqaquim, et al. (2011) "Combined Oral and Intranasal Corticosteroid Therapy: An Advance in the Management of Nasal Polyposis?", Annals of Internal Medicine, 154: 365-367.*
Mukherjee, et al. (2009) "Selective Cancer Targeting via Aberrant Behavior of Cancer Cell-associated Glucocorticoid Receptor", Molecular Therapy, 17(4): 623-31.*
Gabizon, et al. (1990) "Effect of Liposome Composition and Other Factors on the Targeting of Liposomes to Experimental Tumors: Biodistribution and Imaging Studies", Cancer Research, 50: 6371-78.*
Campbell, et al. (2002) "Cationic Charge Determines the Distribution of Liposomes between the Vascular and Extravascular Compartments of Tumors", Cancer research, 62: 6831-36.*
Frisch (2004) E1A as a Tumor Supressor Gene, Clinical Cancer Research, 10: 2905-07.*
Vojtesek, et al. (1993) "Regulation of p53 protein expression in human breast cancer cell lines", Journal of Cell Science, 105: 607-12.*
Grignet-Debrus, et al. (1997) "Potential of Varicella zoster virus thymidine kinase as a suicide gene in breast cancer cells", Gene Therapy, 4(6): 560-69.*
Fanayan, et al. (2000) "Growth inhibition by insulin-like growth factor-binding protein-3 in T47D breast cancer cells requires transforming growth factor-beta (TGF-beta ) and the type II TGF-beta receptor", Journal of Biological Chemistry, 275(50): 39146-51.*
Rebuffat, A, et al. "Selective enhancement of gene transfer by steroid-mediated gene delivery." *Nature Biotechnology* (2001) vol. 19, pp. 1155-1161.
Koster, F., et al. "Progesterone and estradiol enhance lipid mediated transfection of Sk-Br-3 mammarian cancer cells." *International Journal of Molecular Medicine* (2002) vol. 9, No. 6 pp. 617-620.
Koster, F., et al. "Additive effect of steroids and cholesterol on the liposomal transfection of the breast cancer cell line T-47D." *International Journal of Molecular Medicine* (2004) vol. 14, No. 4 pp. 769-772.
Koster, F., et al. "Gentherapie gynako-logischer Malignome." *Gynakologe* (2004) vol. 37 pp. 230-236.
Gruneich., J.A., et al. "Cationic corticosteroid for nonviral gene delivery." *Gene Therapy* (2004) vol. 11, No. 8, pp. 668-674.
da Cruz, M. T. G., et al. "Improving lipoplex-mediated gene transfer into C6 glioma cells and primary neurons." *Experimental Neurology* (2004) vol. 187, No. 1, pp. 65-75.

(Continued)

*Primary Examiner* — Robert M Kelly
(74) *Attorney, Agent, or Firm* — Ladas & Parry LLP

(57) ABSTRACT

The present invention relates to a cationic lipid based aqueous formulation comprising cationic lipid, dexamethasone and a neutral co-lipid, wherein the said formulation is useful for selective targeting and delivering gene to glucocorticoid receptor expressing cancer cells. Glucocorticoid receptors (GR) express in various normal and cancer cells. A lot of ligand activated physiological functions are known involving GR but its role in cancer progression (if any) is not clearly understood. Synthetic GR antagonist, dexamethasone (Dex) finds use as anti-inflammatory drug and is known to induce apoptosis in cancer cells. This Dex is included in a cationic lipid-based formulation as a co-lipid to deliver to and express genes specifically in cancer cells possibly through expressed GR. Gene delivery to cancer cells is independent of the gene construct, and tumor cell line. Normal transformed cells expressing GR but with no cancer lineage show much smaller level of transfection. The composition of the formulation is optimized. The formulation may have particular application to the enhanced delivery of anticancer genetic constructs to cancer, with the synergistic effect of Dex in inducing apoptosis as such.

40 Claims, 8 Drawing Sheets

(56) References Cited

OTHER PUBLICATIONS

Reddy, B. S., et al. "17 Beta-estradiol-associated stealth-liposomal delivery of anticancer gene to breast cancer cells." *Angewandte Chemie* (2005) vol. 44, No. 41, pp. 6723-6727.

Mikherjee, A., et al. "Haloperidol-associated Stealth Liposomes—A Potent Carrier for Delivering Genes to Human Breast Cancer Cells." *The Journal of Biological Chemistry* (2005) vol. 280, No. 16, pp. 15619-15627.

* cited by examiner

AQUEOUS FORMULATION FOR SELECTIVE TARGETING AND DELIVERING GENE TO CANCER CELLS

This is a continuation-in-part of copending International Application PCT/IN2007/000367 filed on Aug. 27, 2007, which designated the U.S., claims the benefit thereof and incorporates the same by reference.

FIELD OF THE INVENTION

The present invention relates to an aqueous formulation useful for selective targeting and delivering of genes to cancer cells, comprising a cationic lipid, a steroid and a neutral co-lipid.

More particularly, the present invention relates to an aqueous formulation useful for enhanced, non-viral, delivery of genetic products to cancer cells, comprising a cationic lipid, a steroid and a neutral co-lipid, wherein the said cationic lipid, a steroid and a neutral co-lipid are mixed in the ratio in the range of 0.75:0.5:1 to 1:2:1 preferably 0.75:1:1 to 1:2:1.

BACKGROUND AND PRIOR ART OF THE INVENTION

Chemotherapy and radiation therapies are two current clinical modalities commonly used for the treatment of cancer. Mostly these techniques are effective to block the growth of a tumor; however, there is often a recurrence of the disease, possibly because of incomplete cell killing or cells acquiring drug resistance.

Glucocorticoid receptor is a nuclear hormone receptor residing in various cells including both cancerous and non-cancerous cells. It has two subtypes alpha and beta. This receptor, a ligand activated transcription factor, upon activation translocates itself into the nucleus. As a homodimer it binds to specific DNA sequences called glucocorticoid response elements (GRE) and positively or negatively regulates transcription of target genes.

Dexamethasone (dex), a potent glucocorticoid acts on intracellular glucocorticoid receptor and regulates transcription of several genes. Several of the glucocorticoids including dex exhibit antiproliferative effect on several tissues of different origin (Corroyer et. al. 1997; Ramalingam et. al. 1997; Rider et. al. 1996; Goya et. al. 1993; Wattenberg and Estensen 1996). These molecules also regulate and control metabolism, development, inflammation, cell growth, proliferation and differentiation (Yamamoto et. al. 1985; Cole et. al. 1995; Rogatsky et al. 1997). In various cancer cells such as in non-small cell lung carcinoma Dex mediates suppression of cellular proliferation through the accumulation of cells in G1/G0 stage of the cell cycle and by hypophosphorylation of retinoblastoma protein (Greenberg et. al. 2002). Glucocorticoid-signaling through glucocorticoid receptors potentiate a possible hypoxia related pathway leading to inflammation. As an anti-inflammatory agent, dex also possesses an important role in inhibiting hypoxia inducible factor (HIF-1), which has direct role in mediating angiogenesis through up-regulation of VEGF (Leonard et. al 2005). Hence, glucocorticoids such as dexamethasone (dex) are a very important and inexpensive drug-like substitute used in various pathological conditions.

There is an example of dexamethasone being structurally modified into a cationic entity by conjugating spermine into it. The cationic dexamethsone-spermine compound is used to complex and transfer genes to airway epithelial with concurrent reduction of inflammation (Gruneich et. al. 2004).

The viral based gene delivery is quite well known and is extensively investigated utilizing their phenomenally efficient process of delivering genes to wide variety of cells. A number of problems including host toxicity, immunogenic responses and non-specific genomic integration of transferred gene make viral delivery a risky option for delivering genes. In comparison, non-viral gene delivery is a much more robust and clinically safe option compared to viral counterparts. The patented cationic lipid, DODEAC (Banerjee et. al. U.S. Pat. Nos. 6,503,945 and 6,436,516), whose structure is N,N-dihydroxyethyl, N,N-dioctadecyl, ammonium chloride forms cationic liposome using co-lipid cholesterol in membrane filtered water. This product has been used for the transfection of DNA into cultured eukaryotic cells of various origins. However, the formulation in spite of exhibiting moderate transfection of genes to all cells irrespective of origin shows no specific targeting of genes to cancer cells expressing glucocorticoid receptor. Towards this end, the present invention relates to development of a new dexamethasone carrying cationic lipid based formulation, which targets and deliver genes to glucocorticoid receptor expressing cancer cells.

Therefore, keeping in view the hitherto known prior art, the inventors of the present invention realized that there exists a need to develop an aqueous formulation useful for selective targeting and delivering gene to cancer cells, comprising a cationic lipid, a steroid and a neutral co-lipid.

The present invention deals with targeted gene delivery which is specific to glucocorticoid receptors of cancer cells only and not of normal cells. The normal cells may be having glucocorticoid receptors but the formulation of the present invention will not target the gene to those normal cells.

OBJECTS OF THE INVENTION

The main, object of the present invention is to provide an aqueous formulation useful for selective targeting and delivering of genes to cancer cells, comprising a cationic lipid, a steroid and a neutral co-lipid.

More particularly, the object of the present invention is to provide an aqueous formulation useful for enhanced, non-viral delivery of genetic products to cancer cells comprising a cationic lipid, a steroid and a neutral co-lipid, wherein the said cationic lipid, a steroid and a neutral co-lipid are mixed in the ratio in the range of 0.75:0.5:1 to 1:2:1 preferably 0.75:1:1 to 1:2:1.

Yet another object of the present invention is to provide a process for the preparation of the said aqueous formulation by formation of small uni-lamellar liposome.

Still another object of the present invention is to provide a pharmaceutical composition comprising the said cationic lipid based formulation complexed with a therapeutic amount of biologically active.

SUMMARY OF THE INVENTION

The present invention provides an aqueous formulation useful for selective targeting and delivering of genes to cancer cells, comprising a cationic lipid, a steroid and a neutral co-lipid.

Accordingly, the present invention provides an aqueous formulation useful for enhanced, non-viral delivery of genetic products to cancer cells comprising a cationic lipid, a steroid and a neutral co-lipid, wherein the said cationic lipid, a steroid and a neutral co-lipid are mixed in the ratio in the range of 0.75:0.5:1 to 1:2:1 preferably 0.75:1:1 to 1:2:1.

In still another embodiment of the present invention, the said cationic lipid used is selected from the group comprising DODEAC (N,N-dihydroxyethyl, N,N-dioctadecyl ammonium chloride), DOTAP (1,2-dioleoyloxypropyl)-N,N,N-trimethylammonium chloride and DMRIE (1,2-dimyristyloxypropyl-3-dimethyl-hydroxy ethyl ammonium bromide).

In still another embodiment of the present invention, the cationic lipid used is preferably DODEAC (N,N-dihydroxyethyl, N,N-dioctadecyl ammonium chloride)

Further in an embodiment of the present invention, the said steroid is selected form the group comprising dexamethasone, predinisolone, fluprednisolone, betamethasone, methylpredinisolone, triamcinolone and hydrocorticosone.

In yet another embodiment of the present invention, the steroid used is more preferably dexamethasone.

In yet another embodiment of the present invention, the said neutral co-lipid used is preferably cholesterol and is capable of enhancing the transfection efficiency of the said formulation up to 4 fold.

In still another embodiment of the present invention, the selective targeting and delivery of gene is achieved by using a non-viral mode.

In yet another embodiment of the present invention, the non viral mode includes biologically active molecules selected from the group comprising ribosomal RNA, antisense poly nucleotide RNA, antisense poly nucleotide DNA, genomic polynucleotide DNA, cDNA, and mRNA encoding anti cancer gene.

In still another embodiment of the present invention, the gene used for selective targeting and delivery is selected from the group consisting of cytotoxic, anti-cancer and anti-metastatic genes.

In yet another embodiment of the present invention, the gene used for selective targeting and delivery is selected from the group comprising p53, tumor necrosis factor Alpha, thymidine kinase, cytosine deaminase, 5 E1A and Tumor growth factor Beta.

In still another embodiment of the present invention, the cancer is selected from the group comprising breast, lung, colon and prostate cancer.

In yet another embodiment of the present invention, the cancer cell lines used are selected from the group comprising A549 (lung), MCF-7 (breast), HT-29 (colon) and PC-3 (prostate).

Further in another embodiment of the present invention, the process for the preparation of an aqueous formulation comprises the following steps of:
(a) preparing liposome by dissolving cationic lipid, a steroid and neutral co-lipid in a mole ratio of 0.75:0.5:1 to 1:2:1 preferably 0.75:1.0:1.0-1:2:1 in a mixture of methanol and chloroform in a glass vial;
(b) removing, the solvent from the mixture obtained from step (a) using a thin flow of moisture-free nitrogen gas;
(c) keeping the lipid film as obtained from step (b) under vacuum for 6-10 hours after drying the film;
(d) hydrating the dried lipid film as obtained from step (c) using sterile deionized water to obtain a liposome having total volume of 1 mL for a time period of 10-15 hours;
(e) vortexing the liposome as obtained from step (d) for 1-2 minutes to remove adhering lipid film followed by sonicating, in a bath sonicator for 2-3 minutes at room temperature to prepare multi-lamellar vesicles;
(f) sonicating the multi-lamellar vesicles with a titanium probe for 1-2 minutes to prepare desired small uni-lamellar vesicles, which is indicated by formation of clear translucent solution;
(g) storing the obtained formulation as obtained from step (f) at 0-4° C. until complexed with a biologically active molecule.

Further in another embodiment of the present invention, the mole concentration of the steroid and the neutral co-lipid is varied in the range of 0.1-5 mole equivalents separately at a fixed mole concentration of cationic lipid.

In still another embodiment of the present invention, freezing and thawing cycles can cause loss of efficiency of the said formulation.

In yet another embodiment of the present invention there is provided a pharmaceutical composition comprising effective therapeutic amount of the said formulation complexed with therapeutically acceptable amount of a biologically active molecule.

In still another embodiment of the present invention, the pharmaceutical composition can be administered in to, a subject, wherein the subject is a mammal including a human.

In yet another embodiment of the present invention, the route of administering the said pharmaceutical composition is selected from the group comprising intra-venous, intra-muscular and intra-peritoneal.

In still another embodiment of the present invention, the said pharmaceutical composition can be alternatively administered into the cancer cells at a ratio of 0.1-0.5 μg of DNA per 50,000 cells in an in vitro system.

In yet another embodiment of the present invention, the ratio of cationic lipid to biological molecule in the pharmaceutical composition is in the range of 1:1 to 8:1.

Further in another embodiment of the present invention, the plasmid used could be of any construction.

DETAILED DESCRIPTION OF THE INVENTION

Figure 1:
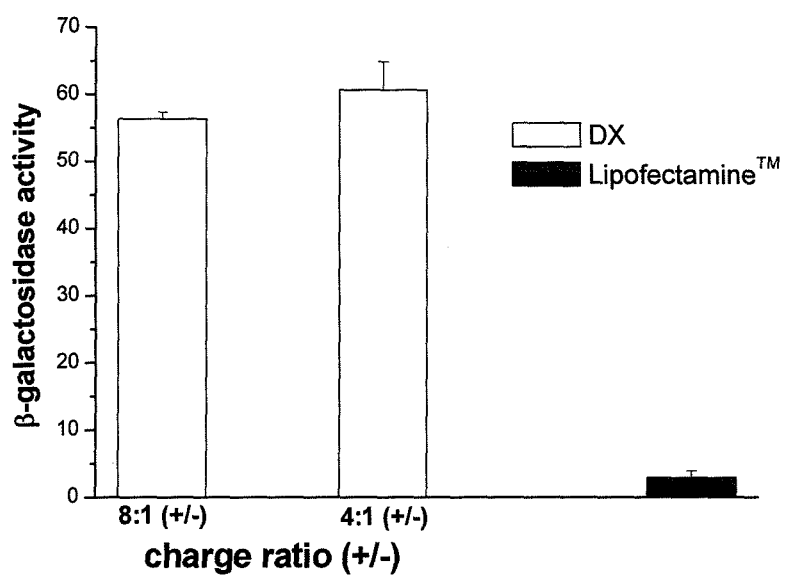
FIG. 1 is a bar graph showing the influence of the dexamethasone associated lipid carrier carrying gene on the expression of a pCMV-β-galactosidase construct in A549 human metastatic lung cancer cells. A549 cells were transfected with a pCMV-β-galactosidase reporter construct (0.3 μg) associated in lipoplex form with respective lipid carriers DX and lipofectamine. β-galactosidase expression was assessed 48 h post transfection. Each value represents the mean±SEM for three identically treated samples.
Figure 2:
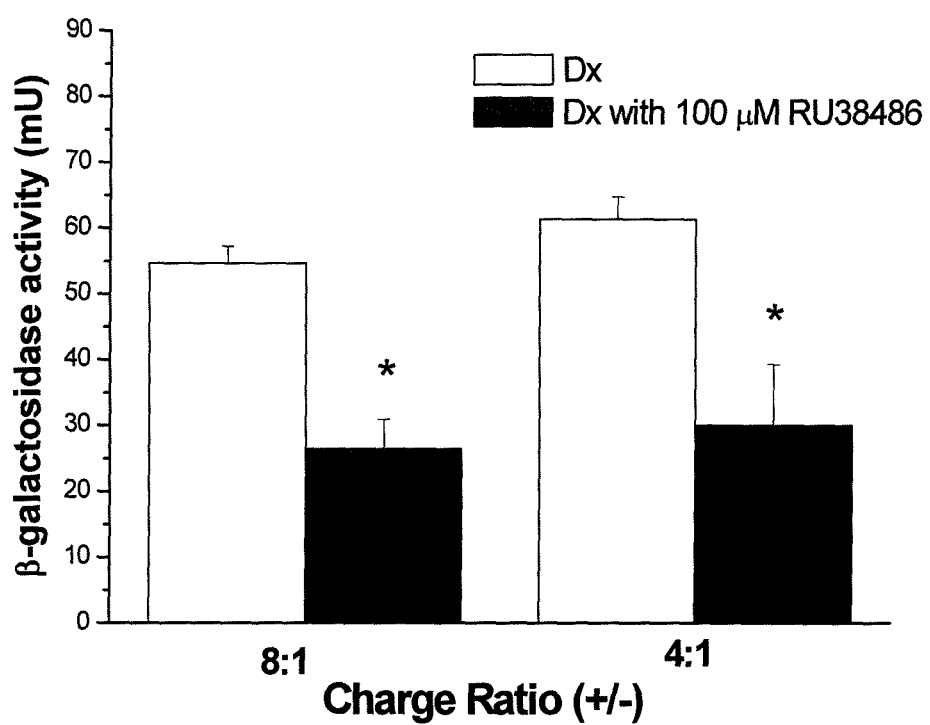
FIG. 2 is a bar graph showing the GR-mediated facilitation of gene delivery to A549 human lung cancer cells. The A549 cells were pretreated with RU-486, a GR antagonist and then transfected with pCMV-β-galactosidase vector complexed in lipid carriers. The β-galactosidase activity was evaluated 48 hr post transfection and expressed β-galactosidase unit per cell. Each value represents the mean±SEM for three identically treated cell wells and * indicates the significant difference between the β-galactosidase value obtained from cells pretreated and untreated with RU-486. ($p<0.01$)

In the present invention, it has been determined that using an glucocorticoid pharmacologic agent in combination with a gene of interest provides a distinct improvement in the efficiency of gene delivery to cells which express glucocorticoid receptors as well as increasing the number of cells receiving the gene. In particular, dexamethasone, one of the most potent synthetic glucocorticoids, at mole ratios up to 3 compared to the cationic lipid, has been shown to facilitate the non-viral gene delivery of a variety of genetic constructs capable of performing their function (including apoptotic cell death) in human cancer cells.

Therefore the present invention provides an aqueous formulation useful for selective targeting and delivery of genes to cancer cells, comprising:
(a) a cationic lipid,
(b) a steroid and
(c) a neutral co-lipid characterized in enhancing the transfection efficiency and stability of the formulation,
wherein the said cationic lipid, steroid and neutral co-lipid are mixed in the ratio in the range of 0.75:0.5:1 to 1:2:1 preferably 0.75:1:1 to 1:2:1.

In a preferred embodiment of the invention, genes which can induce cell death are delivered via a non-viral route combination with glucocorticoid pharmacological compounds in order to provide more complete tumor emission and more effective prevention of tumor recurrence, thus leading to improved patient survival. The glucocorticoid pharmacological agent (e.g., dexamethasone) is to be administered via the same route of gene delivery, by incorporating it with the non-viral gene carrier (e.g., a cationic lipid coat). In this embodiment, four classes of genes may be used. First, cytotoxic genes such a tumor necrosis factor alpha or the tumor suppressor gene p53, which promotes apoptosis, can be provided. Second, genes which sensitize cells by enzymatically activating pro-drugs can be provided. For example, thymidine kinase or cytosine deaminase which respectively activate the cytotoxic pro-drugs gancylclovir and 5-fluorocytosine could be provided. Third, genes which promote immune surveillance could be provided. For example, tumor growth factor-beta 1 could be provided in combination with interleukin-2 and interferon-gamma. Fourth, antimetastatic genes, such as 5 E1A, could be provided.

The idea of making this formulation stems from the fact that dexamethasone, a glucocorticoid, has close structural resemblance with cholesterol, a commonly used co-lipid present in many of the cationic lipids used for non-viral based gene delivery.

The present invention provides a method for delivering genetic constructs via a non-viral mode with enhanced efficiency by co-formulating cationic lipid based gene delivery formulation carrying a glucocorticoid based pharmacologic agent along with the common co-lipid cholesterol.

Cholesterol as a co-lipid has long been used in liposomal formulations. It is known that cholesterol-containing liposomes have greater stability and lower ion-permeability than when cholesterol is not used [Straubinger et al 1983, Cell, 32, 1069-1079]. In the event of lysosomal entrapment during cellular delivery the liposomal cargo is expected to be chewed up by the lysosomal degradative enzymes, such as nucleases, that work at pH<6. It is very much conceivable from the above known facts that cholesterol-associated liposomes not only provide a concrete integrity to the lipid-DNA complex in cytosol but also prevent diffusion of lower pH solution containing lysosomal nucleases inside the lipid-DNA core. The use of cholesterol increasing the stability of the genetic cargo and transfection efficiency is documented previously [Templeton et al. 1997, Nature Biotechnology, 15, 647-652; Xu and Szoka 1996, Biochemistry, 35, 5616-5623].

In the context the present invention stands with complete patentability because the formulation uses our own patented cationic lipid along side a secondary co-lipid dexamethasone, and a common, generic, glucocorticoid. The dexamethasone is not modified at all and is used as such. The concentration at which the dexamethasone is used did not induce any toxicity to non-cancer cells. The use of dexamethasone for the targeted gene delivery to cancer is not documented in any of these papers. Moreover, we for the first time showed that upon associating dexamethasone into cationic lipid formulation, the cancer cells are alone targeted leaving non-cancer cells untouched, even though the glucocorticoid receptors, through which dexamethasone works in cells, are ubiquitously present in all cells.

The following examples are given by the way of illustration of the present invention and should not be construed to limit the scope of the present invention.

Example 1

Figure 3:
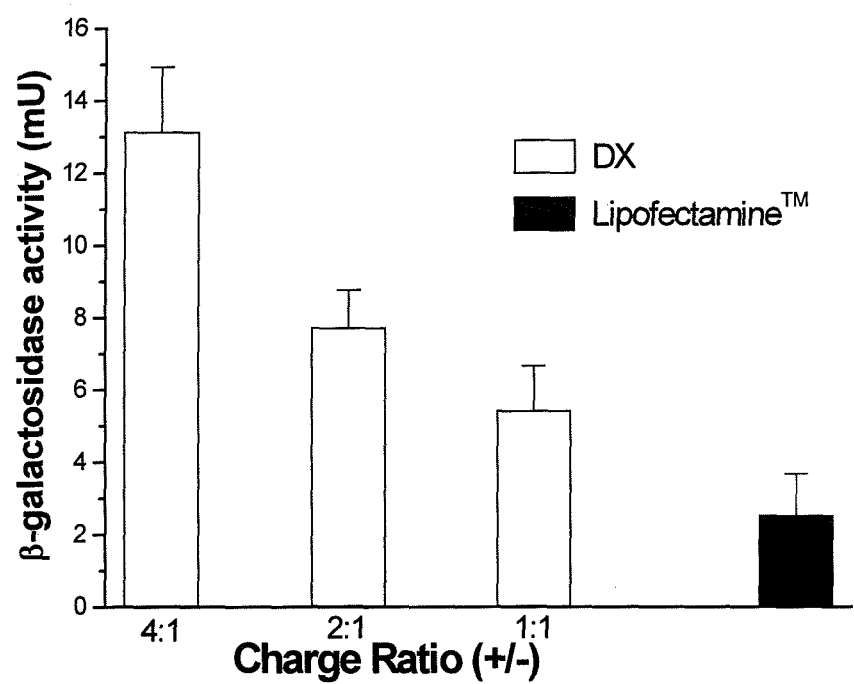
FIG. 3 is a bar graph showing the influence of the dexamethasone associated lipid carrier carrying gene on the expression of a pCMV-β-galactosidase construct in MCF-7 human primary breast cancer cells. MCF-7 cells were transfected with a pCMV-β-galactosidase reporter construct (0.3 μg) associated in lipoplex form with respective lipid carriers DX and lipofectamine. β-galactosidase expression was assessed 48 hr post transfection. Each value represents the mean±SEM for three identically treated samples.
Figure 4:
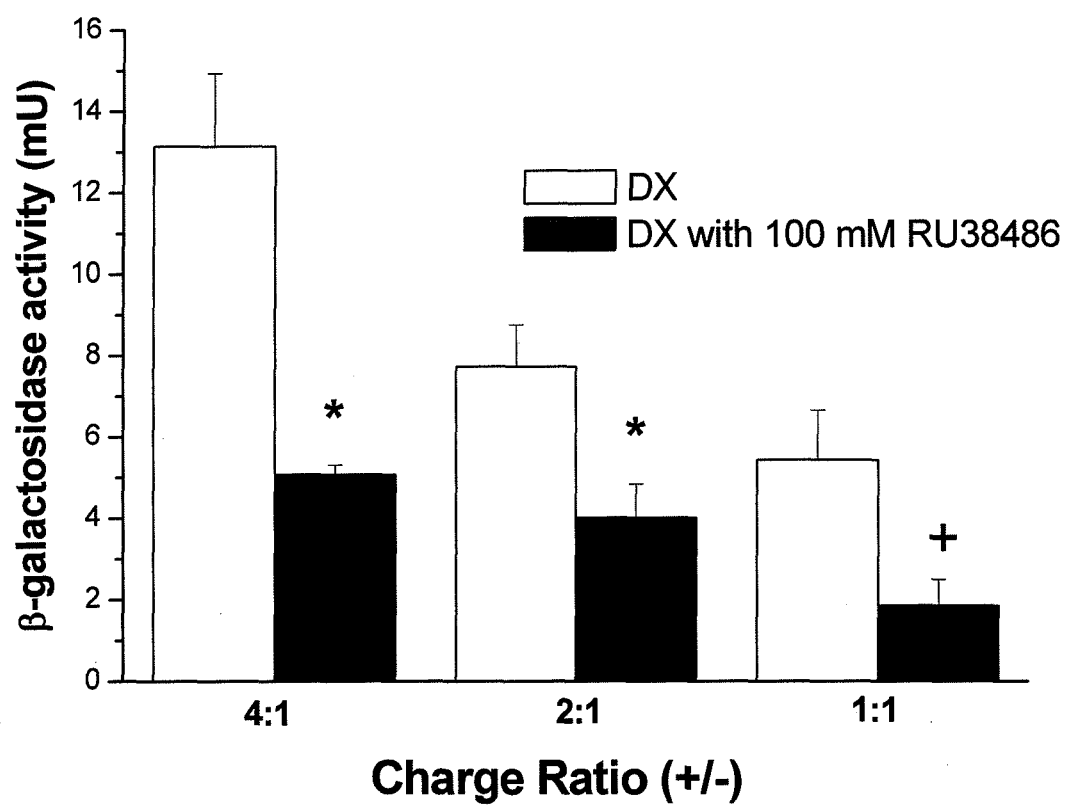
FIG. 4 is a bar graph showing the GR-mediated facilitation of gene delivery to MCF-7 human breast cancer cells. The MCF-7 cells were pretreated with RU-486, a GR antagonist and then transfected with pCMV-β-galactosidase vector complexed in lipid carriers. The β-galactosidase activity was evaluated 48 hr post transfection and expressed as β-galactosidase unit per cell. Each value represents the mean±SEM for three identically treated cell wells and * indicates the significant difference between the β-galactosidase value obtained from cells pretreated and untreated with RU-486. (* p<0.01 and + p=0.0109).

Glucocorticoid Receptor Expressing Cell-Specific Gene Delivery Properties of the Dexamethasone-Cationic Liposomal Formulation The in vitro transfection efficacies of DX liposome containing dexamethasone in combination with DODEAC as cationic lipid and cholesterol as co-lipid at a mole ratio of 0.75:1:1 were evaluated by reporter gene expression assay using pCMV-SPORT-β-gal plasmid as the reporter gene in A549, MCF-7 and CHO cells across the cationic lipid to DNA having charge ratios 8:1 to 1:1. Dexamethasone containing liposome DX has been found to be nearly 2-30 folds more efficient in transfecting A549 and MCF-7 cells (human cancer cells expressing glucocorticoid receptor) (FIGS. 1 and 3) than CHO cell line. DX was most efficient in transfecting lung cancer cells A549 at cationic lipid:DNA charge ratios of 8:1 and 4:1 (FIG. 1). Transfection efficiency of DX in A549 at 2:1 and 1:1 was at least 10-20 fold less than that of other charge ratios. However, DX was most efficient in transfecting breast cancer cells MCF-7 at cationic lipid:DNA charge ratios of 4:1, 2:1 and 1:1 (FIG. 3). Both in A549 and MCF-7 cells, Lipofectamine™ mediate comparatively much less transfection in comparison to DX (FIGS. 1 & 3).

Figure 5:
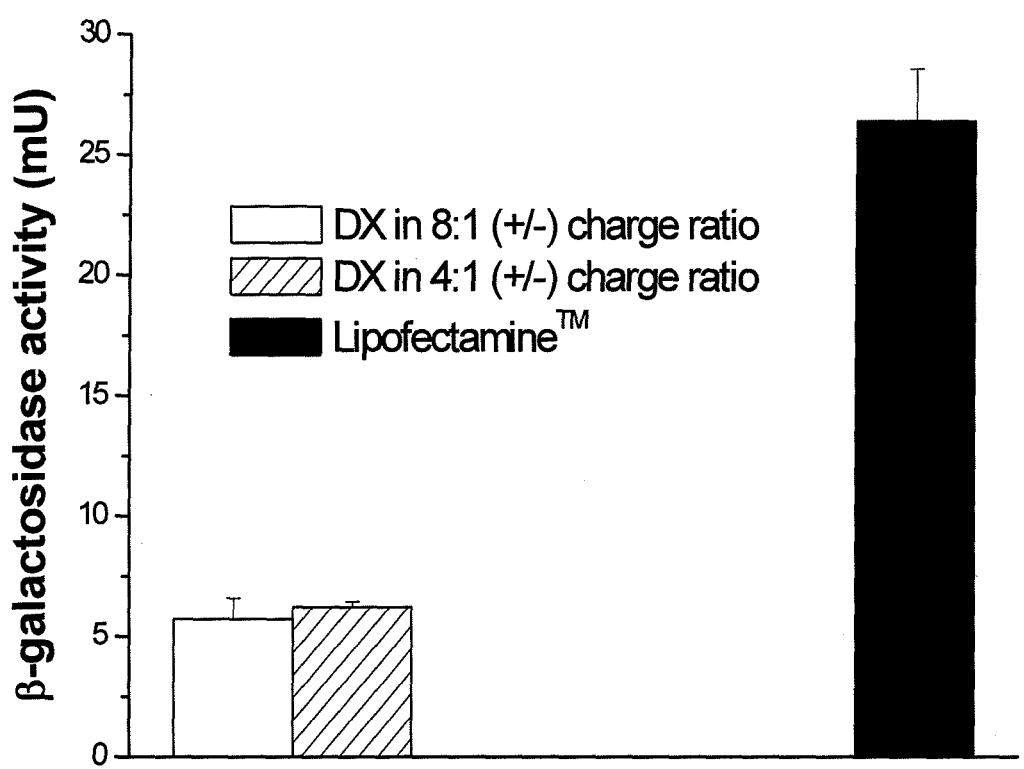
FIG. 5 is a bar graph showing that there is no influence of the dexamethasone associated lipid carrier carrying gene on the expression of a pCMV-β-galactosidase construct in CHO (chinese hamster ovarian) transformed cells, which is in originality not a cancer cell line. CHO cells were transfected with a pCMV-β-galactosidase reporter construct (0.3 μg) associated in lipoplex form with respective lipid carriers DX and lipofectamine. β-galactosidase expression was assessed 48 hr post transfection. Each value represents the mean±SEM for three identically treated samples.
Figure 6:
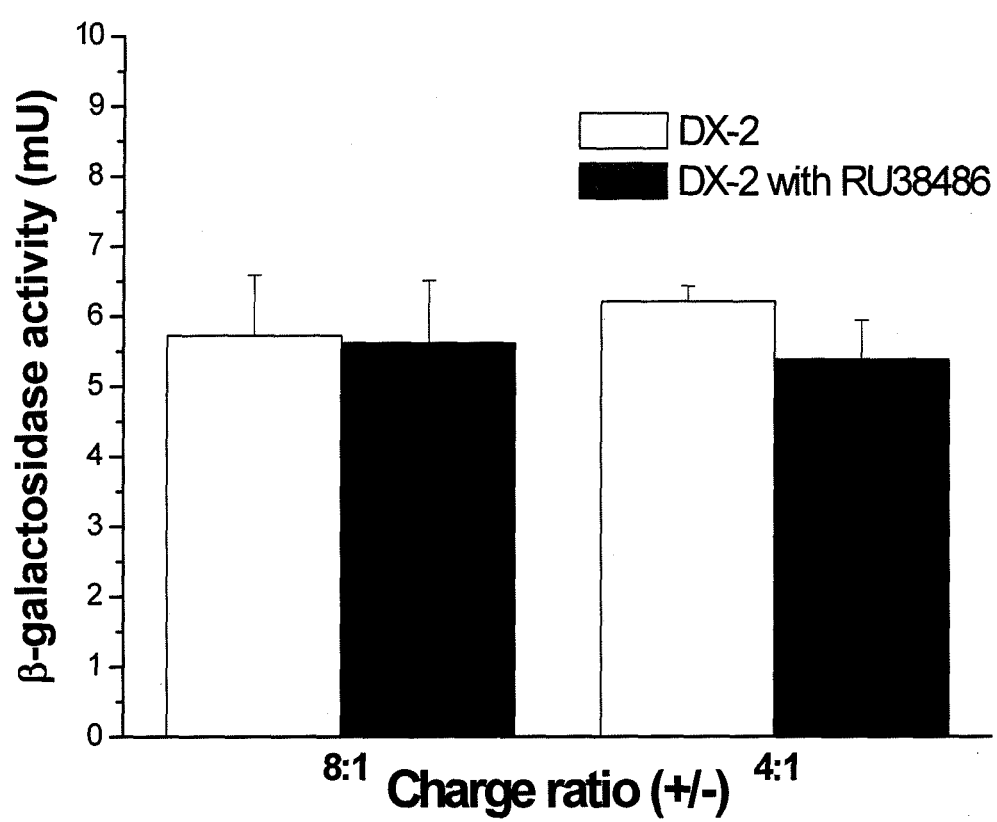
FIG. 6 is a bar graph showing that there is no GR-mediated facilitation of gene delivery to CHO (chinese hamster ovarian) transformed cells, which is in originality not a cancer cell line. The CHO cells were pretreated with RU-486, a GR antagonist and then transfected with pCMV-β-galactosidase vector complexed in lipid carriers. The β-galactosidase activity was evaluated 48 hr post transfection and expressed as β-galactosidase unit per cell. Each value represents the mean±SEM for three identically treated cell wells and, indicates that there is no significant difference between the β-galactosidase values obtained from cells pretreated and untreated with RU-486. (p>0.1).

Significantly low levels of reporter gene expression were observed for DX in the otherwise highly transfectable, non-cancerous, transformed cell CHO across all the charge ratios studied with 8:1 and 4:1 giving the highest transfection efficiencies (FIG. 5). Transfection efficiencies of other charge ratios are not shown. Lipofectamine™ as expected did show up very high transfection efficiency in CHO with respect to DX (FIG. 5). The contrastingly enhanced □-galactosidase reporter gene expression level observed in both A549 and MCF-7 cells (FIGS. 1 and 3) strongly indicate that transfection of glucocorticoid receptor expressing cancer cells, A549 and MCF-7 by DX is likely to be mediated by the glucocorticoid receptor-binding dexamethasone as present in formulation DX.

Example 2

The transfection efficiencies of the DX formulation in transfecting glucocorticoid receptor expressing lung and breast cancer cells were significantly reduced when the gene transfer experiments were carried out by pretreating the cells with the RU-38486, the commercially available glucocorticoid receptor antagonists (FIGS. 2 and 4) (p<0.01). Similar RU-38486 pretreatment studies in CHO cells yielded no significant change in transfection efficiencies (FIG. 6) (p>0.1). Thus, the results summarized in FIGS. 1-6 provided strong evidence for the involvement of glucocorticoid receptors expression in breast and lung cancer cells for the present class of dexamethasone associated gene delivery reagents.

Example 3

Materials used—Dulbecco's Modified Eagle medium (DMEM), fetal bovine serum was obtained from Sigma-Aldrich. Lipofectamine™ was obtained from Invitrogen. p-CMV-.beta.-galactosidase was a generous gift from Dr N. M. Rao, CCMB, India. Dexamethasone, RU-38486 were purchased from (sigma chemical co., St. Louis, Mo.)

Cell-Culture—MCF-7, CHO, A549 cells were purchased from National Center for Cell Sciences (Pune, India) and were mycoplasma free. Cells were cultured in DMEM medium (Sigma Chemical Co., St. Louis, Mo.) containing 10% fetal bovine serum (Sigma Chemical Co., St. Louis, Mo.) and 1% penicillin-streptomycin at 370 C in a humidified atmosphere of 5% CO2 in air. Cultures of 85-90% confluency were used for all of the experiments. The cells were trypsinized, counted, subcultured in 96-well plates for transfection and viability studies. The cells were allowed to adhere overnight before they were used for experiments.

Example 4

Liposome Preparation

All the necessary compounds (for e.g. DODEAC, Cholesterol, DOPE, Dexamethasone) were taken as stock solutions and mixed in a sample vial in appropriate amounts. It was dried as a thin film in gentle nitrogen flow and further dried in high vacuum for 6 hrs. Then it was hydrated for overnight. After that it was subjected to bath sonication for 10-15 min and then probe sonicated at room temperature using a Ti-probe sonicator for 3-4 min to get SUV liposome. The liposomes were kept at 4° C.

Plasmid Complexation & Gene Transfection—

For a typical gene transfection study in vitro, cells were first seeded at a density of 12,000-15,000 cells/well in a 96 well plate usually 18-24 h before transfection. Plasmid DNA was complexed with cationic liposome typically in the following manner: 0.30 μg of pCMV-SPORT-β-gal DNA, a negatively charged entity (diluted to 50 μl with plain DMEM) was electrostatically complexed with varying amount of cationic liposomes (a positively charged entity, diluted to 50 μl with plain DMEM) for 30 min. The molar ratios (lipid:DNA) were 8:1, 4:1, 2:1 and 1:1. After the complexation of plasmid DNA and cationic liposome was completed, 200 μl of DMEM containing 10% FBS (CM1×) were added to the resulting lipoplexes for triplicate experiments. Thus the final concentration of serum became 6.7%. Cells were washed with phosphate-buffered saline (PBS), pH 7.4 (1×200 μl) and then with lipoplex (100 μl). After incubation of the cell plates at a humidified atmosphere containing 5% $CO_2$ at 37° C. for 4 hr, 100 μl of DMEM containing 10% FBS (CM1×) were added to cells. The reporter gene activity was assayed after 48 hr. The media were removed completely from the wells and cells were lysed with 50 μl of 1× lysis buffer (NP-40) for 30 min. The beta-galactosidase activity per well was estimated by adding 50 μl of 2× substrate (1.33 mg/ml of ONPG, 0.2 M sodium phosphate, pH 7.3 and 2 mM magnesium chloride) to the cell-lysate in the 96 well plate. Absorption of the product ortho-nitrophenol at 405 nm was converted to absolute μ-galactosidase units using a calibration curve constructed with commercial μ-galactosidase enzyme.

Example 5

RU 38486 Pretreatment

RU 38486 was dissolved in DMSO at a concentration of 10 mM. 1 μl of it were added to each well plate where cells were plated previously in 100 μl of DMEM+10% FBS. After 2 hr media were removed and cells were washed with PBS (1×100 μl) and treated with lipoplexes.

Statistical Analysis—All experiments were repeated at least once. Data were expressed as mean±standard derivation and statistically analyzed by the two-tailed unpaired Student t-test using the Microsoft Excel software program (Microsoft, Seattle, Wash.). Data were primarily considered significant if p<0.01.

Example 6

Effect of Cholesterol to the Stability of Liposome

Figure 7:
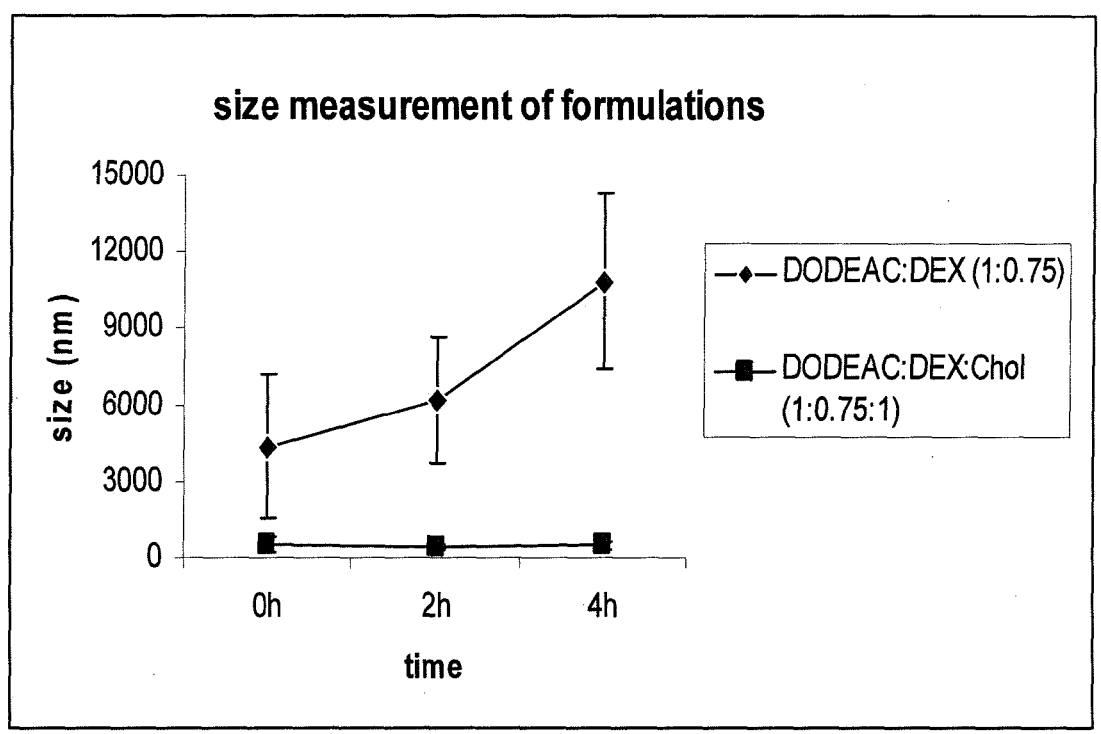
FIG. 7 is a plot of size against time as determined in Example 6.

An experiment has been conducted to prove that indeed the cholesterol inclusion increases the stability of the liposomal formulation. The optimal formulation concentration that we used in our examples was 1:0.75:1 for DODEAC:DEX:Chol. We made a formulation devoid of cholesterol but having the same ratio of cationic lipid and dexamethasone. The new formulation is hence DODEAC:DEX, 1:0.75. The formulations were made 1 mM in concentration with respect to cationic lipid. 50 μl of each formulation was dispersed in 2 ml of phosphate buffer saline (PBS). PBS contains similar ionic strength and pH that prevails in a cellular environment. Then we proceeded to measure the size in Zetasizer (Malvern Instruments, U.K.) over the period of time as indicated in FIG. 7.

The data here indeed proves that the absence of cholesterol in cationic lipid formulation is detrimental for the size-stability of the liposome. The cholesterol-less formulation tends to increase in its size which might render it precipitate out in due course. In fact after 20 h it is noticed that the DODEAC:DEX (1:0.75) formulation indeed precipitated out, while the cholesterol-containing formulation [DODEAC DEX:Cholesterol::1:0.75:1] remained intact and showed no signs of precipitation. The wide range of literature related with cationic lipid mediated, gene transfection shows that the optimal size of the liposome showing efficient transfection should be in submicron level primarily because the lipid formulations with more than micron size will tend to precipitate out in long run rendering them incapable of carrying any bioactive molecules such as DNA in a near-soluble form. Moreover, a very big particulate matter will not be compatible in fusing with cellular membrane and hence will not be able to penetrate the membrane. In the same scenario, our cholesterol-formulated liposome does not change its size showing tremendous amount of stability and structural integrity of the formulation.

Example 7

Effect of Cholesterol to the Efficiency of Transgene Expressions

Figure 8:
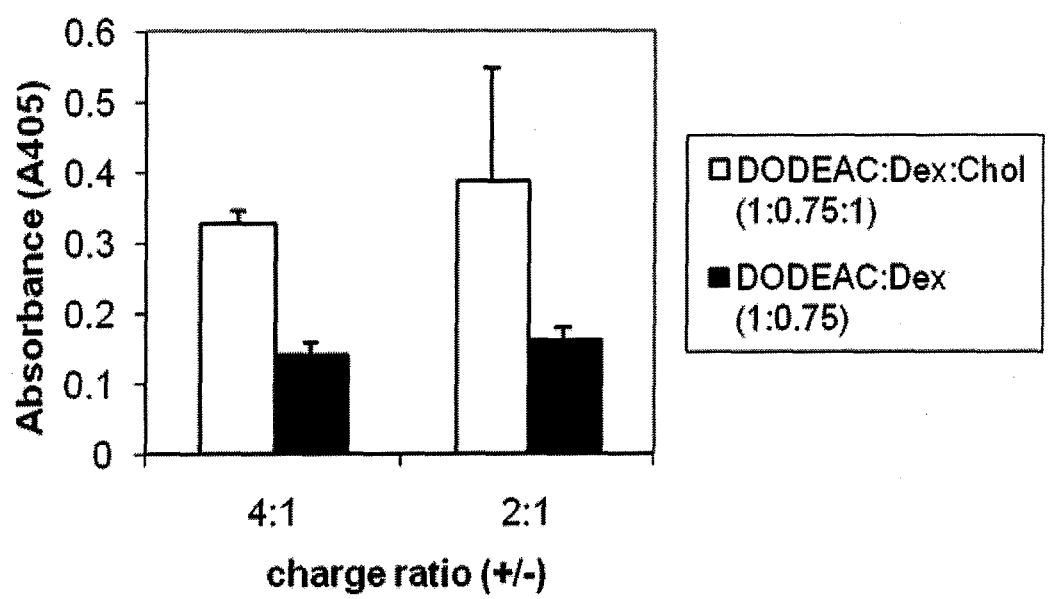
FIG. 8 is a bar graphic showing the effect of cholesterol on the efficiency of transgene expressions as determined in Example 7.

Two dexamethasone (DEX) associated cationic liposome formulations comprising with or without cholesterol (Chol) were made and proceeded to check their gene transfection efficiencies. The formulations were DODEAC:DEX:Chol (1:0.75:1) and DODEAC:DEX (1:0.75). The said formulations were respectively complexed with plasmid encoding β-galactosidase gene and fed to the cells. Following 4 h of lipid/DNA complex treatment the cells were washed and kept at normal cell culture conditions for 48 h, on completion of which the cells were washed, lysed and assayed for the β-galactosidase gene using o-nitrophenol-b-D-galactopyrano side (ONPG) substrate. The formation of o-nitrophenol is measured by measuring absorbance at 405 nm. The efficiency of transfection is directly proportional to the expression of transgene (here, β-galactosidase enzyme) that produces o-nitrophenol upon exposure with ONPG substrate. The results are shown in FIG. 8.

As the result shows that the cholesterol formulated cationic liposome could induce more transfection (2-4 folds) than cholesterol-less formulation.

ADVANTAGES

The process of the present invention can be exploited for preparing cationic lipid based gene transfer reagents containing glucocorticoid receptor binding dexamethasone in the formulation. The invention of this dexamethsone associated cationic lipid based gene delivery vehicle is useful for delivering polyanions, polypeptides or nucleopolymers into cells via glucocorticoid receptors. The formulation disclosed herein can be used to deliver an expression vector into a cell for manufacturing or therapeutic use. The expression vectors can be used in gene therapy protocols to deliver a therapeutically useful protein to a cell or for delivering nucleic acids encoding therapeutically useful protein molecules. The dexamethasone associated lipid based formulation can be formulated with anionic, zwitterionic and lipophilic therapeutic agents including anticancer agents such as doxorubicin hydrochloride, a hydrophilic compound, or Taxol™, a lipophilic compound to obtain complexes comprising the invented dexamethasone-associated formulation and a therapeutic agent(s). In the invented dexamethasone-associated cationic lipid based formulation, two classes of genes may be used. First, cytotoxic genes such a tumor necrosis factor alpha or the tumor suppressor gene p53, which promotes apoptosis, can be provided. Second, those genes can be provided which sensitize cells by enzymatically activating pro-drugs. For example, thymidine kinase or cytosine deaminase, which respectively activates the cytotoxic pro-drugs gancylclovir and 5-fluorocytosine. Third, genes that promote immune surveillance could also be provided. For example, tumor growth factor-beta 1 could be provided in combination with interleukin-2 and interferon-gamma. Fourth, antimetastatic genes, such as 5 E1A, could also be provided for killing metastatic cells.

We claim:

1. An aqueous formulation useful for targeted gene expression in human cancer cells expressing glucocorticoid receptors and delivery of genetic material to said cancer cells, the formulation comprising:
    (a) a cationic lipid,
    (b) a glucocorticoid steroid and
    (c) a neutral co-lipid,
wherein the glucocorticoid steroid improves an efficiency of delivery of the genetic material to human cancer cells expressing glucocorticoid receptors, wherein the cationic lipid, steroid and neutral co-lipid are mixed in a molar ratio in the range of 0.75:0.5:1 to 1:2:1, and wherein the glucocorticoid steroid is selected from the group consisting of dexamethasone, prednisolone, fluprednisolone, betamethasone, methylprednisolone, and triamcinolone.

2. The aqueous formulation according to claim 1, wherein the cationic lipid is selected from the group consisting of DODEAC, DOTAP, and DMRIE.

3. An aqueous formulation according to claim 1, wherein the neutral co-lipid is cholesterol.

4. An aqueous formulation according to claim 1, comprising genetic material selected from the group consisting of cytotoxic genes, prodrug activator genes, immune surveillance promoter genes and anti-metastatic genes.

5. An aqueous formulation according to claim 4, wherein the cytotoxic genes are selected from the group consisting of p53 and tumor necrosis factor alpha.

6. A process for the preparation of the aqueous formulation according to claim 1, the process comprising the following steps of:
    (a) preparing liposome by dissolving the cationic lipid, the steroid and the neutral co-lipid in a mole ratio of 0.75:0.5:1 to 1:2:1 in a mixture of methanol and chloroform in a glass vial;
    (b) removing the solvent from the mixture obtained from step (a) using a thin flow of moisture free nitrogen gas to obtain lipid film;
    (c) keeping the lipid film as obtained from step (b) under vacuum for at least 6 hours after drying the film;
    (d) hydrating the dried lipid film as obtained from step (c) using sterile deionized water to obtain liposome having total volume of at least 1 ml for a time period of 10-14 hours;
    (e) vortexing the liposome as obtained from step (d) for 1-2 minutes to remove adhering lipid film followed by sonicating in a bath sonicator for 2-3 minutes at room temperature to prepare multi-lamellar vesicles;

(f) sonicating the multi-lamellar vesicles with a titanium probe for 1-2 minutes to prepare desired small uni-lamellar vesicles, which is indicated by formation of clear translucent solution; and (g) storing the obtained formulation as obtained from step (f) at 0-4° C. until complexed with biologically active molecule.

7. A process according to claim 6, wherein a mole concentration of the steroid and the neutral co-lipid is varied in the range of 0.1-5 mole equivalents separately at a fixed mole concentration of cationic lipid.

8. A pharmaceutical composition comprising a therapeutic amount of a formulation comprising
(a) a cationic lipid,
(b) a glucocorticoid steroid and
(c) a neutral co-lipid,
the cationic lipid, steroid and neutral co-lipid being mixed in a molar ratio in the range of 0.75:0.5:1 to 1:2:1, wherein the glucocorticoid steroid improves an efficiency of genetic material expression in human cancer cells expressing glucocorticoid receptors, and wherein the glucocorticoid steroid is selected from the group consisting of dexamethasone, prednisolone, fluprednisolone, betamethasone, methylprednisolone, and triamcinolone, said formulation being complexed with a therapeutically acceptable amount of the genetic material.

9. A pharmaceutical composition comprising
(a) a cationic lipid,
(b) a glucocorticoid steroid and
(c) a neutral co-lipid,
the cationic lipid, steroid and neutral co-lipid being mixed in a molar ratio in the range of 0.75:0.5:1 to 1:2:1, said formulation being complexed with a therapeutically acceptable amount of genetic material, wherein the glucocorticoid steroid improves an efficiency of genetic material expression in human cancer cells expressing glucocorticoid receptors, wherein the glucocorticoid steroid is selected from the group consisting of dexamethasone, prednisolone, fluprednisolone, betamethasone, methylprednisolone, and triamcinolone, and wherein the molar charge ratio of cationic lipid to genetic material is in the range of 1:1 to 8:1.

10. A pharmaceutical composition according to claim 8, wherein the genetic material is selected from the group consisting of ribosomal RNA, genomic polynucleotide DNA, cDNA, and mRNA encoding anti cancer gene, wherein said genetic material encodes cytotoxic genes, prodrug activator genes, immune surveillance promoter genes or anti-metastatic genes.

11. The aqueous formulation according to claim 2 wherein the cationic lipid is DODEAC.

12. The aqueous formulation according to claim 1, wherein the steroid is dexamethasone.

13. The aqueous formulation according to claim 4 comprising prodrug activator genes selected from the group consisting of thymidine kinase and cytosine deaminase.

14. The aqueous formulation according to claim 4 comprising an immune surveillance promoter gene that is tumor growth factor beta 1.

15. The aqueous formulation according to claim 4 comprising an anti-metastatic gene that is adenovirus type 5 EIA.

16. The aqueous formulation according to claim 4 comprising genetic material selected from the group consisting of ribosomal RNA, genomic polynucleotide DNA, cDNA, and mRNA encoding anti cancer gene, wherein the genetic material encodes cytotoxic genes, prodrug activator genes, immune surveillance promoter genes or anti-metastatic genes.

17. The pharmaceutical composition according to claim 8 wherein the cationic lipid is selected from the group consisting of DODEAC, DOTAP and DMRIE.

18. The pharmaceutical composition according to claim 8 wherein the cationic lipid is DODEAC.

19. The pharmaceutical composition according to claim 8, wherein the steroid is dexamethasone.

20. The pharmaceutical composition according to claim 8 wherein the neutral co-lipid is cholesterol.

21. The pharmaceutical composition according to claim 8 wherein the genetic material is selected from the group of genes consisting of cytotoxic genes, prodrug activator genes, immune surveillance promoter genes and anti-metastatic genes.

22. The pharmaceutical composition according to claim 21 comprising cytotoxic genes selected from the group consisting of p53 and tumor necrosis factor alpha.

23. The pharmaceutical composition according to claim 21 comprising prodrug activator genes selected from the group consisting of thymidine kinase and cytosine deaminase.

24. The pharmaceutical composition according to claim 21 comprising an immune surveillance promoter gene that is tumor growth factor beta.

25. The pharmaceutical composition according to claim 21 comprising an anti-metastatic gene that is adenovirus type 5 EIA.

26. A pharmaceutical composition according to claim 9, wherein the genetic material is useful for delivery of cytotoxic genes, prodrug activator genes, immune surveillance promoter genes and is selected from the group consisting of ribosomal RNA, antisense poly nucleotide RNA, antisense poly nucleotide DNA, genomic polynucleotide DNA, cDNA, and mRNA encoding anti cancer gene.

27. The pharmaceutical composition according to claim 9 wherein the cationic lipid is selected from the group consisting of DODEAC, DOTAP and DMRIE.

28. The pharmaceutical composition according to claim 9 wherein the cationic lipid is DODEAC.

29. The pharmaceutical composition according to claim 9, wherein the steroid is dexamethasone.

30. The pharmaceutical composition according to claim 9 wherein the neutral co-lipid is cholesterol.

31. The pharmaceutical composition according to claim 9 wherein the genetic material is selected from the group of genes consisting of cytotoxic genes, prodrug activator genes, immune surveillance promoter genes and anti-metastatic genes.

32. The pharmaceutical composition according to claim 31 comprising cytotoxic genes selected from the group consisting of p53 and tumor necrosis factor alpha.

33. The pharmaceutical composition according to claim 31 comprising prodrug activator genes selected from the group consisting of thymidine kinase and cytosine deaminase.

34. The pharmaceutical composition according to claim 31 comprising an immune surveillance promoter gene that is tumor growth factor beta.

35. The pharmaceutical composition according to claim 31 comprising an antimetastatic gene that is adenovirus type 5 EIA.

36. The aqueous formulation according to claim 1, wherein the glucocorticoid steroid is prednisolone.

37. The aqueous formulation according to claim 1, wherein the glucocorticoid steroid is fluprednisolone.

38. The aqueous formulation according to claim 1, wherein the glucocorticoid steroid is betamethasone.

39. The aqueous formulation according to claim 1, wherein the glucocorticoid steroid is methylprednisolone.

40. The aqueous formulation according to claim 1, wherein the glucocorticoid steroid is triamcinolone.

\* \* \* \* \*